United States Patent
Farber et al.

(10) Patent No.: US 11,339,502 B2
(45) Date of Patent: May 24, 2022

(54) COMBINATORIAL DERIVATIVES OF OLIGOPEPTIDES HAVING ANTIVIRAL PROPERTIES

(71) Applicants: Boris Slavinovich Farber, Moscow (RU); Sof'ya Borisovna Farber, Moscow (RU)

(72) Inventors: Boris Farber, Brooklyn, NY (US); Sof'ya Farber, Brooklyn, NY (US); Artur Viktorovich Martynov, Kharkov (UA)

(*) Notice: Subject to any disclaimer, the term of this patent is extended or adjusted under 35 U.S.C. 154(b) by 0 days.

(21) Appl. No.: 16/771,467

(22) PCT Filed: Jun. 16, 2017

(86) PCT No.: PCT/RU2017/000426
§ 371 (c)(1),
(2) Date: Jun. 10, 2020

(87) PCT Pub. No.: WO2018/231093
PCT Pub. Date: Dec. 20, 2018

(65) Prior Publication Data
US 2021/0071318 A1    Mar. 11, 2021

(51) Int. Cl.
*C40B 40/10*    (2006.01)
*A61K 38/00*    (2006.01)

(52) U.S. Cl.
CPC .............. *C40B 40/10* (2013.01); *A61K 38/00* (2013.01)

(58) Field of Classification Search
None
See application file for complete search history.

(56) References Cited

U.S. PATENT DOCUMENTS

2012/0129760 A1* 5/2012 Martynov .............. C12P 21/06
435/68.1

* cited by examiner

*Primary Examiner* — Christian C Boesen
(74) *Attorney, Agent, or Firm* — Daniel M. Cohn; Howard M. Cohn

(57) ABSTRACT

Field of application: The invention relates to organic and bioorganic combinatorial chemistry, namely, to new combinatorial libraries of derivatives oligopeptides and supramolecular structures based on them, which when used without separation into individual components possess powerful antiviral properties.
The essence of the invention: The invention is based on the task of synthesizing combinatorial derivatives of oligopeptides with antiviral properties and with a new mechanism of action, the use of which will significantly increase the effectiveness of treatment and reduce the treatment time for viral diseases such as influenza, herpes virus infections.

8 Claims, 4 Drawing Sheets
Specification includes a Sequence Listing.

COMBINATORIAL DERIVATIVES OF OLIGOPEPTIDES HAVING ANTIVIRAL PROPERTIES

TECHNICAL FIELD

The invention relates to organic and bioorganic combinatorial chemistry, namely, to new combinatorial libraries derivatives of oligopeptides and supramolecular structures based on them, which, when used without separation into individual components, possess powerful antiviral properties.

STATE OF THE ART

Viral diseases account for more than 90% of all registered infectious diseases. But there are very few antiviral drugs introduced into pharmaceutical industry. Such substances often have toxic properties, a small spectrum of action, and decreased response and resistance effect quickly develops to them. Therefore, the development of antiviral agents that would not have toxic properties, were effective in the treatment of a wide range of viral infections, is an urgent task of modern medicine.

Currently there are very few substances are known that would be effective at all stages of a viral infection. Most of the known this type of substances interferons and their inducers, but there are no such substances and are not yet known which would combine the healing and antiviral properties against of widespread viral diseases—HIV/AIDS, herpes, influenza and multiple others. Rimantadine is mainly known for treatment for influenza. This substance, which blocks only the stage of penetration of the virus into the cell and the early stage of specific reproduction and it does not affect the pathogenesis of the disease. Long-term use of this drug is impossible, because it has neurotropic effects and can cause hallucinations, it can impair brain function due to inhibition of impulse conduction along the nerve fiber.

Leukocyte α-interferon among other substances effective in the treatment of influenza. Leukocyte α-interferon is a protein which synthesized in activated human white blood cells. It has the ability to cause resistance to influenza in epithelial cells of the nasopharynx. But its healing properties are very insignificant. It is ineffective on the 2nd-6th day of the flu and is a preventive measure. Recombinant interferons are expensive and often lead to allergic reactions. In addition, with the development of the disease, the effectiveness of interferon therapy decreases, and the resistance of the virus to interferon increases.

The closest prototype of the substance that is patented are modified proteins and these modified proteins used for control of viral infections. These proteins like albumin, lactoferrin, transferrin, lactalbumin are going through process with various anhydrides and acylating agents. The authors also patented the mechanism of action of these proteins—inhibition of viral adhesion. These proteins should have a molecular weight of more than 60,000 with little variation. A significant prophylactic antiviral effect of these proteins was shown in experiments on cell cultures. Substances showed activity against HIV viruses (human and monkey), influenza, cytomegalovirus, poliovirus, Selmiki forest virus, Sendai virus, parainfluenza, Coxsackie virus. The authors showed that acylated proteins are non-toxic and can protect animals against infection with viruses.

The prototype has several drawbacks: it is a purely prophylactic agent (such proteins did not have a therapeutic effect on cells that are already infected with the virus) and does not have therapeutic properties in infected animals. Due to the fact that the prototype is a high molecular weight protein, it can be used only for parenteral use, the drug is an individual high molecular weight compound, not oligopeptides and it is not a dynamic self-organizing supramolecular system and, therefore viruses will quickly adapt and become resistant to the drug.

Also known is a patent [1], which describes modified peptides with antiviral properties and a method for their preparation, characterized in that the main active substance is a mixture (ensemble) of oligopeptides—products of protein hydrolysis with changed to opposite the charges of the molecules, and to obtain them, a partial hydrolysis of the protein-containing feed is carried out first, and then a chemical modification of the sum of the obtained oligopeptides is carried out with the charge of their molecules being replaced with the opposite and the composition of the obtained oligopeptides is used as an antiviral agent.

This is sum of modified oligopeptides can inhibit the activity of the β-importin heterodimer of the cell and inhibit the replication of viruses whose replication cycle depends on the functions of the nucleus. An ensemble of modified oligopeptides based on a dynamic self-organizing system is more effective in the treatment of viral infections, such as influenza, herpes, viruses of animal diseases at all stages of the development of the infectious process, when other drugs are ineffective. The tool has a wide spectrum of action, is slightly toxic and available for industrial use and manufacturing, it is effective at all stages of the virus replication cycle, which dependent on the cell nucleus.

The disadvantages of the analogue include the impossibility of standardizing the series of the drug, validation of analysis methods, the inconstancy of the composition and pharmacological effects and the instability of the pharmacological effect due to the short half-life in the animal organism. These disadvantages are eliminated by increasing the degrees of freedom of the self-organizing system of peptides (increasing the number of derivatives in the mixture) by simultaneously modifying the structure of the peptides with two modifiers at once. This leads to an increase in the number of derivatives by at least two orders of magnitude. In addition, instead of natural peptides and enzymatic hydrolysis, our invention proposes to initially use nuclear localization signal peptides involved in the transfer of the viral genome to the nucleus as a target. This type preparation with known amino acid sequence, known mechanism of action, is easily standardized in composition and pharmacological activity, as well as analysis methods. The method of binary modification of oligopeptides was not previously known and has never been used to obtain self-organizing combinatorial structures.

DISCLOSURE OF INVENTION

The basis of the invention is the task to synthesize combinatorial derivatives of oligopeptides with antiviral properties and with a new mechanism of action, the use of which will significantly increase the effectiveness of treatment and reduce the treatment time for viral diseases, such as influenza, herpes virus infections. The problem is solved by the synthesis of combinatorial derivatives of oligopeptides with antiviral properties, wherein combinatorial derivatives of oligopeptides, in the structure of which amino group residues are available for modification lysines, histidines, arginines, as well as alcohol residues of threonine and serine available for modification, are simultaneously combinatorial modified with at least two different covalent modifiers and the resulting combinatorial mixture entirely without purification and without isolation of each individual derivative is used as an antiviral agent in various pharmaceutical compositions. The molar ratio of the components of the combinatorial reaction can be calculated according to the formulas:

$$k = n \times (2^n - 1) \quad (1)$$

$$m = 4 \times (3 \times 2^{n-2} - 1) \quad (2)$$

where
n=the number of substitutional groups in the oligopeptide;
m=the number of moles of the original oligopeptide and the number of different molecules of its combinatorial derivatives after synthesis;
k=the number of moles of each of the two modifiers in the combinatorial synthesis reaction to obtain the maximum number of different derivatives.

As covalent modifiers of the structure of oligopeptides in combinatorial synthesis can be used such combinations: at least anhydrides of two dicarboxylic acids, at least anhydrides of two tricarboxylic acids, at least one tricarboxylic anhydride and one dicarboxylic anhydride, for alkylation can be at least two halogen derivatives are used. The combinatorial modification is carried out by simultaneous alkylation with at least one halogen derivative and acylation with one dicarboxylic or tricarboxylic acid anhydride; combinatorial modification is carried out by simultaneous alkylation with a halogen derivative and acylation with dicarboxylic or tricarboxylic acid anhydride.

As oligopeptides, a classic nuclear localization signal (cNLS) can be used, consisting of one or two clusters of positively charged amino acid residues: KK/RXK/R or K/RK/R-X10-12 (K/R) 3/5, where X is any amino acid. Also, as an oligopeptide, a peptide consisting of two clusters of positively charged amino acid residues can be used: KKRKRKRKR (SEQ ID NO:1).

The oligopeptides of the present invention can be produced synthetically or, if necessary, recombinantly by standard methods. Specific embodiments of the oligopeptides are described in detail in the experimental section below. Preferably, the oligopeptides of the invention are prepared by standard chemical synthesis methods, such as, for example, described by Merrifield (J. Am. Chem. Soc. (1963) 85: 21492154).) On the other hand, the (oligo) peptides of the present invention can be produced using methods for cloning and expression of recombinant DNA into a microorganism/host or a cell carrying a DNA fragment, sequence. nucleic acids encoding one of the above peptides. The nucleic acid encoding the sequences can be prepared synthetically, or can be obtained from existing nucleic acid sequences by site-specific mutagenesis.

These nucleic acid sequences can then be cloned into a suitable expression vector and transformed or transfected into a suitable host cell, such as E. coli, Bacillus, Lactobacillus, Streptomyces, mammalian cells (such as CHO, HEK or COS1 cells), yeast (e.g. Saccharomyces, Schizophyllum), insect cells or viral expression systems, such as baculovirus systems. A person skilled in the science will recognize methods for creating nucleic acid sequences and providing means for allowing their expression.

It is also possible to incorporate non-naturally occurring amino acids (such as D-amino acids) into peptides through genetic engineering methods. Then, the peptide can be separated from the host cell culture. This can be achieved by general protein purification and isolation methods that are available in the art. Such methods may, for example, include immunoadsorption or chromatography. It is also possible to provide peptides with a label (such as a histidine tag) during synthesis, which allows for fast binding and purification, after which the label is enzymatically removed to obtain the active peptide.

If the peptide cannot be encoded or expressed, but it is very similar to a peptide that can be encoded or expressed, then a method can be used to preparing a peptide that the peptide resembles, followed by one or more steps in which the aforementioned peptide is modified by chemical or enzymatic methods to prepare the final peptide. Oligopeptides can also be obtained by cleaving the oligopeptide from a larger peptide using proteolytic enzymes like pepsin, papain, etc.

Oligopeptides can also be obtained by cleaving the oligopeptide from a larger peptide using proteolytic enzymes like pepsin, papain, etc. Some more complete entities of the methods that can be used in the preparation of peptides are described in: W. F. Anderson, Nature 392 Supp., 30 Apr. 1998, p. 2530; Pharmaceutical Biotechnology, Ed. D. J. A. Crommelin and R. D. Sindelar, Harwood Academic Publishers, 1997, p. 5370, 167180, 123152, 820; Protein Synthesis: Methods and Protocols, Ed. R. Martin, Humana Press, 1998, p. 1442; SolidPhase Peptide Synthesis, Ed. G. B. Fields, Academic Press, 1997, p. 1780; Amino Acid and Peptide Synthesis, Oxford University Press, 1997, p. 189. New peptides according to any one of the claims can be quickly made by a person skilled in that technology.

Terminology

Alkylation—the introduction of an alkyl substituent in an organic compound molecule. Typical alkylating agents are alkyl halides, alkenes, epoxy compounds, alcohols, less often aldehydes, ketones, esters, sulfides, diazoalkanes. The alkylation catalysts are mineral acids, Lewis acids, and also zeolites. Alkylation is widely used in the chemical and petrochemical industries.

An ensemble or supramolecular ensemble is a term from supramolecular chemistry. The objects of supramolecular chemistry are supramolecular ensembles built spontaneously from complementary, i.e., having geometric and chemical matching of fragments, like spontaneous assembly of complex spatial structures in a living cell [1,2]. Due to the fact that in the synthesis of one oligopeptide in the presence of two modifiers, more than 1500 different derivatives are synthesized, between them molecules necessarily form intermolecular ionic and hydrogen bonds. Such supramolecular structures have significantly higher biological activity than the original peptide. The experiment confirmed the efficacy of the drug in influenza, herpes, in vivo and in ovo models, as described below. We used a combinatorial mixture of oligopeptides in the form of a supramolecular ensemble without separation into separate components.

Acylation—the introduction of the acyl residue of RCO— (acyl) into the organic compound, as a rule, by replacing the hydrogen atom, the introduction of the residue of acetic acid CH3CO— is called acetylation, benzoic C6H5CO— benzoylation, formic HCO— formylation. Depending on the atom to which the acyl residue is attached, C-acylation, N-acylation, O-acylation are isolated. Acid halides and acid anhydrides are used as acylating agents.

The combinatorial library [lat. combinare—connect, combine; Greek biblion—book and theke—repository]—a set of a large number of various chemical compounds, proteins, genes or oligonucleotides, which allows quickly search for target genes or target proteins. For example, a kit consisting of millions of different chemicals, or a set of recombinant DNA molecules, obtained by incorporating various antibodies into the light and heavy chains of a cDNA vector, etc.

Combinatorial synthesis—synthesis by methods of combinatorial chemistry, involves the simultaneous reaction between three or more reagents with the formation of a combinatorial synthesis product, consisting of dozens of derivatives. These derivatives are then separated chromatographically, confirm their structure and study the biological activity.

Simultaneous combinatorial modification with two modifiers—if a multifunctional molecule with more than two groups available for modification is used in the combinatorial synthesis reaction and two modifying agents are immediately introduced into the reaction, for example, acetic anhydride and succinic anhydride. As a result of the reaction, a mixture of acylated derivatives in different positions—acetyl-succinyl derivatives—is formed.

Therapeutically effective amount—for the purposes of the present description, refers to the amount of the drug, which is the combinatorial derivative of the oligopeptide according to the present research invention. It is sufficient for the manifestation of antiviral activity, for different viruses, animal models, where the amount may differ.

THE BEST EMBODIMENT OF THE INVENTION

Example 1. Obtaining a Combinatorial Mixture of the Oligopeptide KKRKRKRKR (SEQ ID NO:1) (Hereinafter KR)

Preliminarily, the KKRKRKRKR (SEQ ID NO:1) oligopeptide is prepared using a standard peptide synthesizer technique or by genetic engineering.

1 Mmol of KKRKRKRKR (SEQ ID NO:1) oligopeptide is dissolved in 50 ml of phosphate buffered saline, 3 Mmol of succinic anhydride and 3 Mmol of phthalic anhydride are added, and the solution is stirred until both anhydrides are completely dissolved. The solution is poured into vials, lyophilized and used for analysis and research. The calculation of the molar ratios of two modifiers to the oligopeptide is carried out according to the formulas:

$$k = n \times (2^n - 1) \tag{1}$$

$$m = 4 \times (3 \times 2^{n-2} - 1) \tag{2}$$

n=number of substitutional groups in the oligopeptide (n=9);
m=the number of moles of the original oligopeptide and the number of different molecules of its combinatorial derivatives after synthesis (from the same source peptide, 1532 different derivatives are formed both in the places of substitutions and in permutations);
k=the number of moles of each of the two modifiers in the combinatorial synthesis reaction to obtain the maximum number of different derivatives (k=4599)

In this case, the molar ratio to obtain the maximum number of different derivatives (1532 different molecules) is 3:3:1 (succinic anhydride:phthalic anhydride:oligopeptide KKRKRKRKR (SEQ ID NO:1)).

Figure 1:
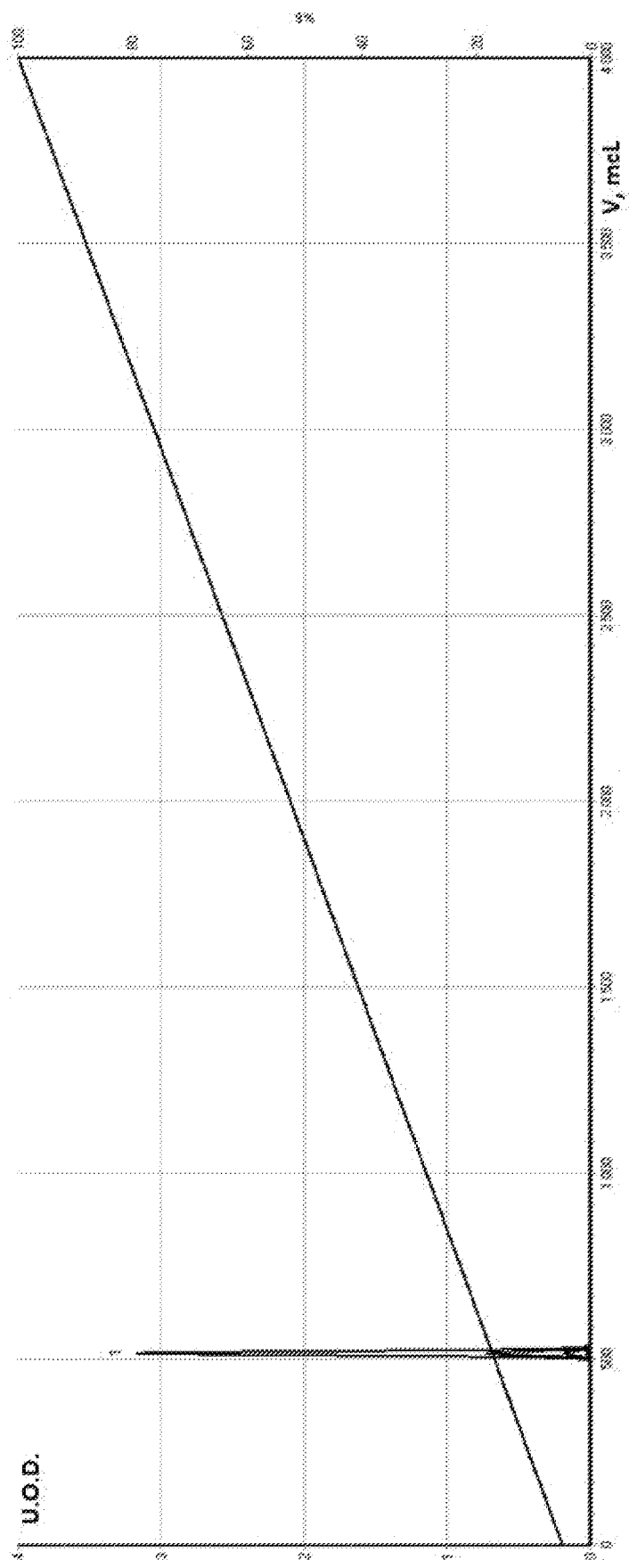
FIG. 1.—HPLC of the original peptide with the amino acid sequence KKRKRKRKR (SEQ ID NO:1) (chromatographic conditions: gradient separation under buffer A conditions: 0.1 M perchloric acid/1 M lithium perchlorate; buffer B: acetonitrile from 5% to 100%; Milichrom A-02 chromatograph, column prontosil-18)

In FIG. 1. shows the result of HPLC analysis of the starting peptide KKRKRKRKR (SEQ ID NO:1). The original peptide when using the detector in the region of 280 nm gives one absorption band.

Figure 2:
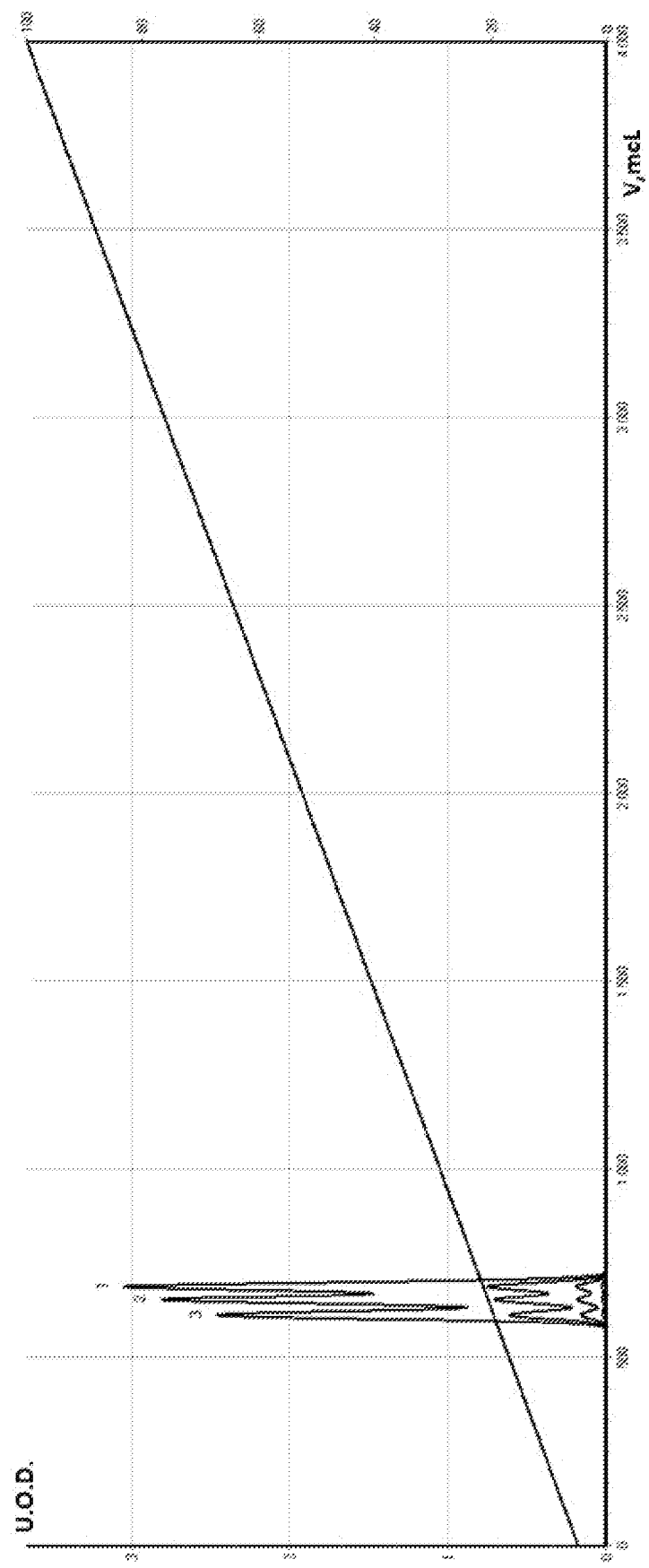
FIG. 2.—HPLC of a combinatorial derivative peptide with the amino acid sequence KKRKRKRKR (SEQ ID NO:1) (chromatographic conditions: gradient separation under buffer A conditions: 0.1 M perchloric acid/1 M lithium perchlorate; buffer B: acetonitrile from 5% to 100%; Milichrom A-02 chromatograph, column prontosil-18).

In FIG. 2. shows the result of HPLC analysis of a combinatorial derivative of the peptide KKRKRKRKR (SEQ ID NO:1). As can be seen from the chromatogram, the peptide peak is not only located in another place—in the region of a more hydrophilic region, it is still broadened, divided into 3 additional bands. This suggests that between 1532 different derivatives of the peptide there are intramolecular/supramolecular bonds of ionic and hydrogen characters that are not able to be broken during the HPLC separation under the classical conditions of gradient HPLC. Using thin layer chromatography and capillary gel electrophoresis, it was also not possible to separate the supramolecular derivative into separate fragments. To modify the peptide, other combinations of at least two different modifiers can be used: carboxylic and polycarboxylic acid anhydrides, carboxylic acid halides, halocarbons. As peptides, one individual oligopeptide can be used as well as oligopeptide mixtures obtained both by the standard method using peptide synthesizers and by genetic engineering methods and using recombinant technology.

To check the biological (antiviral) activity of the synthesized derivatives with different ratios of components in the combinatorial synthesis reaction, the antiviral activity of the derivatives was studied by the screening models of H1N1 influenza virus (Inf), a reference strain of vesicular stomatitis virus (Vesic. —VVS) and herpes simplex virus type 1 (Herp. —strain L-2) in tablets on chicken fibroblast culture according to the degree of degradation (cytopathic effect, detachment from the bottom of the hole).

TABLE 1

Antiviral activity of supramolecular combinatorial derivatives of the oplicigopeptide KKRKRKRKR (SEQ ID NO: 1) obtained in the reaction with a different molar ratio of modifiers

| | The molar ratio of reagents * | | | % cytoprotective antiviral activity ** | | |
|---|---|---|---|---|---|---|
| No. p/p | m | k1 | k2 | Inf | Herp | Vesic |
| 1 | 1532 | 18396*** | 1 | 0 | 0 | 0 |
| 2 | 1532 | 9198 | 4 | 0 | 0 | 0 |
| 3 | -//- | 4599 | 9 | 0 | 0 | 0 |

TABLE 1-continued

Antiviral activity of supramolecular combinatorial derivatives of the oplicigopeptide KKRKRKRKR (SEQ ID NO: 1) obtained in the reaction with a different molar ratio of modifiers

| No. p/p | The molar ratio of reagents * | | | % cytoprotective antiviral activity ** | | |
|---|---|---|---|---|---|---|
| | m | k1 | k2 | Inf | Herp | Vesic |
| 4 | -//- | 2299 | 18 | 0 | 0 | 0 |
| 5 | -//- | 1149 | 36 | 0 | 0 | 0 |
| 6 | -//- | 575 | 72 | 0 | 0 | 0 |
| 7 | -//- | 287 | 143 | 0 | 0 | 0 |
| 8 | -//- | 143 | 287 | 0 | 0 | 0 |
| 9 | -//- | 72 | 575 | 0 | 0 | 0 |
| 10 | -//- | 36 | 1149 | 0 | 0 | 0 |
| 11 | -//- | 18 | 2299 | 0 | 0 | 0 |
| 12 | -//- | 9 | 4599 | 0 | 0 | 0 |
| 13 | -//- | 1 | 9198 | 0 | 0 | 0 |
| 14 | -//- | 0 | 18396*** | 0 | 0 | 0 |
| 16 | -//- | 9198*** | 9198*** | 0 | 0 | 0 |
| 17 | -//- | 4599 | 4599 | 100 | 100 | 100 |
| 18 | -//- | 2299 | 2299 | 50 | 50 | 50 |
| 19 | -//- | 1149 | 1149 | 25 | 25 | 25 |
| 20 | -//- | 575 | 575 | 0 | 0 | 0 |
| 21 | -//- | 287 | 287 | 0 | 0 | 0 |
| 22 | -//- | 143 | 143 | 0 | 0 | 0 |
| 23 | -//- | 72 | 72 | 0 | 0 | 0 |
| 24 | -//- | 36 | 36 | 0 | 0 | 0 |
| 25 | -//- | 18 | 18 | 0 | 0 | 0 |
| 26 | -//- | 9 | 9 | 0 | 0 | 0 |
| 27 | -//- | 1 | 1 | 0 | 0 | 0 |
| 28 | -//- | 18396*** | 0 | 0 | 0 | 0 |
| 29 | -//- | 9198 | 0 | 0 | 0 | 0 |
| 30 | -//- | 4599 | 0 | 0 | 0 | 0 |
| 31 | -//- | 2299 | 0 | 0 | 0 | 0 |
| 32 | -//- | 1149 | 0 | 0 | 0 | 0 |
| 33 | -//- | 575 | 0 | 0 | 0 | 0 |
| 34 | -//- | 287 | 0 | 0 | 0 | 0 |
| 35 | -//- | 143 | 0 | 0 | 0 | 0 |
| 36 | -//- | 72 | 0 | 0 | 0 | 0 |
| 37 | -//- | 36 | 0 | 0 | 0 | 0 |
| 38 | -//- | 18 | 0 | 0 | 0 | 0 |
| 39 | -//- | 9 | 0 | 0 | 0 | 0 |
| 40 | -//- | 1 | 0 | 0 | 0 | 0 |
| 41 | -//- | 0 | 18396*** | 0 | 0 | 0 |
| 42 | -//- | 0 | 9198 | 0 | 0 | 0 |
| 43 | -//- | 0 | 4599 | 0 | 0 | 0 |
| 44 | -//- | 0 | 2299 | 0 | 0 | 0 |
| 45 | -//- | 0 | 1149 | 0 | 0 | 0 |
| 46 | -//- | 0 | 575 | 0 | 0 | 0 |
| 47 | -//- | 0 | 287 | 0 | 0 | 0 |
| 48 | -//- | 0 | 143 | 0 | 0 | 0 |
| 49 | -//- | 0 | 72 | 0 | 0 | 0 |
| 50 | -//- | 0 | 36 | 0 | 0 | 0 |
| 51 | -//- | 0 | 18 | 0 | 0 | 0 |
| 52 | -//- | 0 | 9 | 0 | 0 | 0 |
| 53 | -//- | 0 | 1 | 0 | 0 | 0 |
| 54 | -//- | 0 | 0 | 0 | 0 | 0 |

\* m is the number of moles of the KKRKRKRKR oligopeptide in the combinatorial synthesis reaction; K1 is the number of moles of succinic anhydride in the reaction; K2 is the number of moles of phthalic anhydride in the reaction;
\*\* % of the remaining monolayer of cells after infection with viruses and replacing the culture with the studied drug in the culture after 48 hours of incubation in the presence of the test substance added in a pre-selected concentration (ED90 = 0.05 µg/ml);
\*\*\*the maximum molar ratio at which all groups in the oligopeptide are replaced, an excess of this ratio leads to the fact that unreacted modifiers remain in the reaction medium - succinic anhydride and phthalic anhydride.

As can be seen from the table, only with the calculated ratio of components, when the maximum number of different oligopeptide derivatives is formed, a biologically active and effective supramolecular structure (derivative 17 or KR) capable of completely protecting the cell monolayer ($ED_{100}$) from a dose of 0.05 µg/ml from the degrading cytopathic effect of viruses.

Example 2. Obtaining a Combinatorial Mixture of the Oligopeptide KKRKSTRKR (SEQ ID NO:2) (Hereinafter KR2)

Preliminarily, the KKRKSTRKR (SEQ ID NO:2) oligopeptide is prepared using a standard peptide synthesizer technique or by genetic engineering.

1 Mmol of KKRKSTRKR (SEQ ID NO:2) oligopeptide is dissolved in 50 ml of phosphate buffered saline, 3 Mmol of succinic anhydride and 3 Mmm of maleic anhydride are added, and the solution is stirred until both anhydrides are completely dissolved. The solution is poured into vials, lyophilized and used for analysis and research. The calculation of the molar ratios of two modifiers to the oligopeptide is carried out according to the formulas:

$$k = n \times (2^n - 1) \quad (1)$$

$$m = 4 \times (3 \times 2^{n-2} - 1) \quad (2)$$

n = number of substitutional groups in the oligopeptide (n=9);
m = the number of moles of the original oligopeptide and the number of different molecules of its combinatorial derivatives after synthesis (from the same source peptide, 1532 different derivatives are formed both in the places of substitutions and in permutations);
k = the number of moles of each of the two modifiers in the combinatorial synthesis reaction to obtain the maximum number of different derivatives (k=4599)

In this case, the molar ratio to obtain the maximum number of different derivatives (1532 different molecules) is 3:3:1 (succinic anhydride:phthalic anhydride:KKRKSTRKR (SEQ ID NO:2) oligopeptide).

Figure 3:
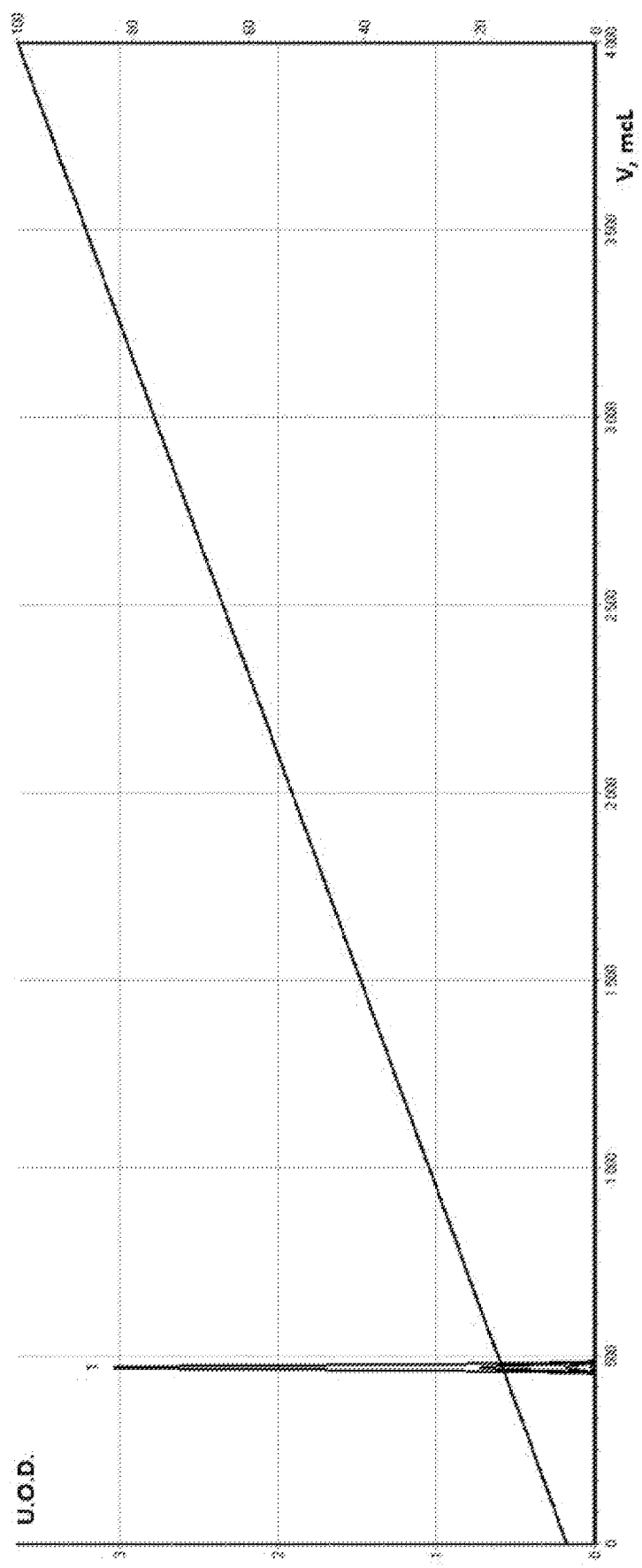
FIG. 3.—HPLC of the original peptide with the amino acid sequence KKRKSTRKR (SEQ ID NO:2) (chromatographic conditions: gradient separation under buffer A conditions: 0.1 M perchloric acid/1 M lithium perchlorate; buffer B: acetonitrile from 5% to 100%; Milichrom A-02 chromatograph, column prontosil-18)

In FIG. 3. shows the result of HPLC analysis of the original peptide KKRKSTRKR (SEQ ID NO:2). The original peptide when using the detector in the region of 280 nm gives one absorption band.

Figure 4:
FIG. 4.—HPLC of a supramolecular combinatorial derivative peptide (SKP) with the amino acid sequence KKRKSTRKR (SEQ ID NO:2) (chromatographic conditions: gradient separation under buffer A conditions: 0.1 M perchloric acid/1 M lithium perchlorate; buffer B: acetonitrile from 5% to 100%; chromatograph Milichrom A-02, column prontosil-18).

In FIG. 4. shows the result of HPLC analysis of the combinatorial derivative peptide KKRKSTRKR (SEQ ID NO:2). As can be seen from the chromatogram, the peak of the peptide is not only located elsewhere—in a more hydrophilic region, it is still broadened, divided into 4 additional bands. This suggests that between 1532 different derivatives of the peptide, there are intramolecular/supramolecular bonds of ionic and hydrogen nature, which are not able to be broken during HPLC separation under classical gradient HPLC conditions. Using thin layer chromatography and capillary gel electrophoresis, it was also not possible to separate the supramolecular derivative into separate fragments. To modify the peptide, other combinations of at least two different modifiers can be used: carboxylic and polycarboxylic acid anhydrides, carboxylic acid halides, halocarbons. As peptides, one individual oligopeptide can be used as well as oligopeptide mixtures obtained both by the standard method using peptide synthesizers and by genetic engineering methods using recombinant technology.

The following types of transplantable cells of human and animal origin were used to determine the maximum tolerated concentration (MIC) in toxicological experiments and study the antiviral activity of the drug KR:

TC—transplantable cells of the kidney of the cattle embryo;
Tr—tracheal cells of the cattle embryo;
Ner-2—transplantable cells of human larynx cancer;
Hela—transplantable cancer cells of the uterus;
Chicken embryos Cells were grown in 199 medium supplemented with 10% bovine serum and antibiotics (penicillin and streptomycin).

Influenza viruses (H3N2), vesicular stomatitis (Indiana strain), coronavirus (X 343/44) and herpes simplex virus type 1 (strain L-2) were used as test viruses. The studies were carried out according to the methods recommended by the State Pharmacological Center of the Ministry of Health of Ukraine.

Example 2. The Study of Toxicity and Determination of the MIC of the Drug KR on Cell Cultures and Chicken Embryos Two-day cell cultures with a well-formed cell monolayer were used to determine BMD. The drug KR tested on four types of the above cells in 5 repetitions. In each experiment, at least 10 test tubes of each culture were used for the study. After removal of the growth medium from the tubes, 0.2 ml of the test solution and 0.8 ml of the supporting nutrient medium were added. Tubes with cells were incubated at 37° C. for 7-8 days.

Controls are tubes with cell cultures into which the drug was not added. The results were taken into account by the presence or absence of a cytopathic effect on cells when viewed under a microscope at low magnification ×10. The degree of cytotoxic action was determined by changing the morphology of cells (rounding and wrinkling of cells, rejection of degenerated cells from the glass) using the four-plus system from + to ++++.

The maximum tolerated concentration was determined by the maximum amount of a substance that did not cause a cytopathic effect on the cells. For this, in various dilutions of the drug in a dose of 0.2 ml was introduced into the cell culture.

To study in vivo toxicity in various doses of the drug in a volume of 0.2 ml, 9-10 day old chicken embryos (5 embryos per MP dilution) were introduced into the allantoic cavity using the following method:

It was taken 10-11-day-old embryos, ovoscopied, and put a pencil mark on the air bag on the side opposite to the location of the embryo, where there are fewer blood vessels. The marked place was disinfected with an alcoholic solution of iodine, then the shell was punctured here and 0.1 ml of material was injected into the hole with a tuberculin syringe. To enter the allantoic cavity, the syringe needle was injected to a depth of 10-15 mm parallel to the longitudinal axis of the egg. After infection, the hole was again disinfected with an iodine alcohol solution, sealed with paraffin and placed for incubation in a thermostat at a temperature of 35-37° C. for 72 hours. Before opening, the embryos were placed for 18-20 hours in a refrigerator at a temperature of 40° C. to maximize the narrowing of blood vessels. After that, the eggs were placed on the tray with the blunt end up, the shell above the air bag was disinfected with an alcoholic solution of iodine and 96% ethanol, then they were broken and removed with sterile tweezers. The membrane lining the bottom of the air sac was also removed, having previously separated it from the underlying chorion-allantoic membrane. After 24 and 48 hours of incubation in a thermostat at 37° C., the number of living and normally developing embryos was taken into account. Calculation of LD50 and MTD was carried out according to the Kerber method.

As a result of studies on various cultures, it was found that KR is non-toxic to cell cultures at a dose of more than 50 mg/ml. (to increase the concentration, the drug was lyophilized and then diluted to 5% concentration). The results of the study of toxicity in different cultures are presented in table 2.

TABLE 2

| | The toxicity of KR in cell cultures | |
|---|---|---|
| No. n/n | Cell culture | MEC (mg/ml) |
| 1 | PT | more than 50 |
| 2 | Tr | -//- |
| 3 | Hep-2 | -//- |
| 4 | Hela | -//- |

The MEC for KR-treated cell cultures is over 50 mg/ml

Example 3. The Study of the Antiviral Effect of the Drug KR2 on Influenza A Virus (N3 N2)

Aqueous solutions of KR in various doses (ten-fold dilutions) were administered to 15 chicken embryos in the allantoic cavity in a volume of 0.2 ml 12 hours after the virus was introduced in a working dose (100 TCD50/0.2 ml).

Each experiment was accompanied by control of the test virus in the working dose. Infected and non-infected (control) embryos were incubated at 360° C. for 48 hours. Then, the embryos were opened, from which the allantoic fluid was aspirated. Titration of the virus in allantoic fluid was carried out according to the generally accepted method with 1% red blood cells of 0 (1) human blood group. Defined coefficient of protection (KZ). The virus titer in the experimental and control groups of chicken embryos is presented in table 3.

TABLE 3

| Effective concentration of KR2 in a model of influenza infection in ovo | | | | |
|---|---|---|---|---|
| | | Virus titer (lg TCID 50/ml) | | Minimum effective concentration |
| Group | The concentration of the drug (mg/ml) | experiment | control | (MEC mg/ml) |
| Control (0.9% sodium chloride solution was injected) | — | 12 | 12 | — |
| Experimental group | 50 ± 5 | 0 | 12 | 0.05 |
| | 5 ± 1 | 0 | 12 | |
| | 0.5 ± 0.05 | 2 | 12 | |
| | 0.05 ± 0.005 | 4 | 12 | |
| | 0.005 ± 0.0005 | 6 | 12 | 5 |

As can be seen from table 3, the minimum effective concentration of KR2 against influenza virus, which completely inhibits the synthesis of the virus, is 0.05 mg/ml. With increasing dilution of the drug, the effectiveness of KR2 decreases and has a dose-dependent character. This fact indicates the presence of a direct antiviral effect of the drug KR2 in relation to the H3N2 influenza virus.

Example 4. The Study of the Antiviral Effect of the Drug KR on Cytopathic Viruses (Vesicular Stomatitis Virus, Coronavirus, Herpes Simplex Virus Type 1)

Antiviral activity against this group of viruses was determined in a culture of the above cells. The reaction was carried out in the following way: 0.2 ml of the corresponding virus in a working dose (100 TCID 50/0.2 ml) was added in a volume of 0.2 ml in a 2-day washed cell culture. 0.8 ml of support medium was added. When the CPP appeared in the culture, the drug KR was introduced in various doses. As a control, the same was done with test viruses without the drug. Cells were incubated at 37° C. in an incubator. The experience was recorded on 3.5.7 days.

The decrease in virus titer under the influence of the test drug by 2 lg or more in comparison with the control was evaluated as a manifestation of antiviral activity. The results of a study of the antiviral activity of the drug KR are presented in table 4

TABLE 4

The study of the antiviral effect of the drug KR against viruses: vesicular stomatitis, coronavirus, herpes simplex virus type 1)

| A drug | Virus | MEC, mg/ml | The maximum drop in the titer of the virus, lg TClD 50/ml |
|---|---|---|---|
| KR | VSV | 0.05 | 3.9 |
|  | CV | 0.05 | 2.9 |
|  | HSV1 | 0.05 | 4.9 |

As can be seen from table 4, KR has antiviral activity and the ability to suppress the reproduction of all the viruses studied by us at a concentration of 0.05 mg/ml with MPC=50 µg/ml. HTI drug is 1000. In addition, KR was active against all the viruses studied, while no single reference drug showed such activity. Thus, the drug is not associated with specific characteristics of the virus or cell culture, but affects the mechanisms common to all cells.

Example 5. The Study of the Antiviral Effect of KR2 In Vitro on Models of Viruses of Farm Animals The tests were carried out in 96-well plastic panels with pig transmissible gastroenteritis virus (TGS) strain D-52 with an initial titer of 104.0 TCID 50/ml (tissue cytopathic doses) in a transplanted piglet test cell culture (PTP) and large diarrhea virus cattle strain "Oregon" with an initial titer of 1070 TTZs5o/ml in transplanted culture of saiga kidney cells (PS).

When testing the viral-static (inhibitory) action, cell cultures were infected with viruses at doses of 100 and 10 TCID ed/ml and incubated in an incubator at 37° C. KR2 was introduced into the cell cultures (CC) at various doses 1-1.5 hours after infection (after adsorption period). For each dilution took 8 holes. After making the compound, the cell cultures were incubated at 37° C. for 72-144 hours until a clear manifestation of CPD (cytopathogenic effect) in the control of viruses.

Controls were viral infected cell cultures, inactive KK and KK, where only different concentrations of KR2 were added. Virusstatic effect was determined by the difference in titer of viruses in the experiment and control.

When determining the virucidal (inactivating) effect, different doses of the compound solution were mixed in equal volumes with virus-containing material and incubated in an incubator at 37° C. for 24 hours. A virus-containing material was used as a control, to which a placebo (saline) and inactive cell cultures were added instead of a compound solution. The mixtures after contact were titrated in parallel with the control. The results were taken into account 72-144 hours after incubation at 37° C., after a clear manifestation of CPD in virus controls. The virucidal effect was determined by the difference in titer of viruses in the experiment and control and expressed in lg TCID 50.

As a result of the studies, it was found that the compound KR2 at a concentration of 40 µg/ml inhibited the reproduction of the TGS virus by 2.75 lg $TCID_{50/mL}$, at an infectious dose of 100 $TCID_{50/mL}$ and in the same dose by 3.75 lg $TCID_{50/mL}$, an infectious dose of 10 $TCID_{50/mL}$. At a dose of 40 µg/ml, KR2 inactivated the TGS virus on 2.0 lg TCD50/ml. Compound KR at a dose of 40 µg/ml inactivated the diarrhea virus KRSna Z, 5 18 $TCID_{50/mL}$.

Thus, the KR2 compound has a viral-static (inhibitory) and virucidal (inactivating) effect on TGS viruses and cattle diarrhea, and chemo drugs can be created on its basis for the treatment and prevention of infectious diseases of viral etiology.

Example 6. The Study of the Antiviral Activity of KR in an Animal Experiment (Herpes Virus Kerato-Conjunctivitis/Encephalitis in Rabbits)

The features of the experimental system and the level of its adequacy to a natural human disease undoubtedly play a decisive role in assessing the effect of antiviral substances on the course of infection. Herpetic experimental infection is of interest due to the fact that herpetic diseases are widespread and extremely variable in clinical manifestations. Models of experimental herpes in animals are finding wider application in the study of new antiviral substances.

As you know, one of the clinical forms of systemic herpes is herpetic encephalitis, which is reproduced in guinea pigs, hamsters, rats, mice, rabbits, dogs, monkeys.

Herpetic keratoconjunctivitis in rabbits with an average weight of 3.5 kg was obtained by applying infectious material (herpes simplex virus type 1 strain L-2) on a scarified cornea. The animal was fixed, anesthesia of the eye was performed with dikain (instilled into the eye). Eyelids were opened, several scratches were applied to the cornea with a syringe needle. Then the virus-containing material was introduced and, closing the eyelids, rubbed it into the cornea in circular motions. Dose of the virus: 0.05 ml. 16 rabbits were used in the experiment, ten of them were injected with KR (daily from the second day of infection −14 days at a dose of 20 mg/kg, and six-placebo (0.9% sodium chloride).

After infection of the HSV1 rabbits, the condition of the cornea, the presence of keratoconjunctivitis, encephalic disorders and the presence of HSV1 antigens in the peripheral blood lymphocytes by the RIF method before and after infection were monitored daily. Prior to infection, all animals in the lymphocytes lacked specific luminescence, which indicated the absence of type 1 herpes virus antigens in the peripheral blood. On day 3 after infection in all animals, the HSV1 antigen was determined in the blood, IF=70%. In addition, three rabbits (two from the experimental group before treatment and one from the control group) developed encephal manifestations—convulsive syndrome, lack of appetite. All animals developed keratoconjunctivitis. On the 4th day after infection, the experimental group of rabbits was injected into the ear vein KR at a dose of 20 mg/kg body weight, and a 0.9% sodium chloride solution was administered to the control group. Every day for two weeks, this procedure was repeated once a day. In the experimental group, all animals survived, and the HSV1 antigen in the blood was not determined on days 13-14. In addition, in the experimental group, encephal manifestations disappeared by the 7th day of drug administration, while in the control 2 animals died. By the 14th day of treatment, one animal died in the experimental group, while in the control—6. Accordingly, the efficacy index was 83.3%, indicating a high therapeutic efficacy of KR in the model of herpetic keratoconjunctivitis/encephalitis in rabbits. In addition, the rabbits in the experimental group gained weight and all animals showed no signs of keratoconjunctivitis. The chemotherapeutic index for rabbits for KR was 1000, which indicates the promise of KR as a highly effective antiviral drug with a wide spectrum of action and low toxicity.

Example 7. The Effect of the Drug KR on Broilers Cross Cobb-500

The purpose of the tests was to study the effect of the drug KR on the reproduction of vaccine virus strains by reducing the titer of the corresponding specific antibodies. It is known that many antiviral drugs, suppressing the reproduction of live vaccine strains of viruses, inhibit the synthesis of specific antiviral antibodies. This effect is associated with the insufficient intensity of the infectious process caused by the vaccine in the bird's body and a weak immune response. It is also known that in many cases, for example, with infectious bursal disease, the use of a live vaccine leads to the induction of synthesis of such an excess titer of antibodies that the bursa is depleted, the bird becomes sensitive to other viruses, there is a decrease in weight gain and an increase in mortality. The use of the drug KR was supposed to show the presence of antiviral properties in several ways: reduction of the excess level (titers) of antibodies, decrease in mortality (safety), increase in weight gain.

In the experiment, broilers were taken on days 36 and 41 for 15 animals per group. KR was drunk the day before vaccination with live vaccines against IBD, Gamboro disease (HD) and infectious bronchitis (IB). In the control were birds that were not fed KR, but were vaccinated. Tables 5-6 show the research results.

TABLE 5

The gain of broilers (at the time of slaughter) in the experimental and control groups

| Index | Weight gain**, +% | Safety**, +% |
|---|---|---|
| Experimental group (n = 15) | 5.0 ± 0.5* | 1.0 ± 0.2* |
| Control Group (n = 15) | -1.2 ± 0.2* | -2.1 ± 0.3* |

*against unvaccinated control, which was taken as a basis.
**(P = 0.01)

As can be seen from table 5, in the experimental group, the weight gain of animals increased by (5.0±0.5)% against weight reduction in the control group vaccinated but not treated (−1.2±0.2)%. Also in the experimental group there was an increase in safety by (1.0±0.2)%.

Table 6 shows the changes in titers of specific antiviral antibodies in the KR-treated vaccination group, the untreated group and the unvaccinated group.

TABLE 6

Change in antibody titer against IBD, BG and IB in vaccinated groups and unvaccinated control

| | The average change in the titer of specific antibodies, ± T | | |
|---|---|---|---|
| | IBD | BG | IB |
| Experimental group (vaccinated and treated with KR) (n = 15) | −1000 ± 400 | −600 ± 200 | −1100 ± 400 |
| Control group No. 1 (vaccinated but not treated with KR) (n = 15) | +2800 ± 700 | +3400 ± 1200 | +2800 ± 1000 |
| Control group (untreated and not vaccinated) | | 0 | |

As can be seen from table 6, KR has a direct (non-immunostimulating) effect against all three viruses. The greatest inhibitory effect was observed in the group with infectious bronchitis—reduction of antibody titer by 1200 units. In the vaccinated, but untreated control, antibody titers increased from 2800 units to 3400 units, indicating an effective process of reproduction of the live vaccine in the bird. Therefore, the use of KR will make it possible to increase broiler weight gain by 5% and reduce mortality by 1%.

KR has a direct antiviral effect, inhibiting the reproduction of viruses of infectious bursal disease, Gumboro disease and infectious bronchitis. KR allows moderate suppression of the replication of vaccine viruses, providing an adequate level of protective antibodies and preventing the depletion of the immunity of birds and a corresponding decrease in weight gain and an increase in mortality.

Example 8. The Study of the Effect of KR on the Effectiveness of Vaccination of Broilers with Live Vaccines The effect of KR on vaccination efficiency was carried out directly in the poultry farm during broiler rearing. In the pathological study of broilers, characteristic changes were observed for colibacteriosis, coccidiosis, and numerous hemorrhages on the mucous membranes of the direct section of the intestine, in the area of the transition of the glandular stomach into the muscular, socaleal glands. The contents of the glandular stomach were stained green. The death of broilers reached about 15-20%. In the study of broiler blood serum at 38-42 days of age, specific titers of antibodies to the New Castle disease virus (BNK) were found to be higher than the protective ones (1:1024, 1:2048) in the hemagglutination inhibition reaction (HSCA).

Study of the Effect of KR at a Dose of 0.03 ml/kg Live Weight on the Effectiveness of Vaccination Against BNK. For this, One of the Houses was Taken for Control, the Others were Experienced (Table 7).

TABLE 7

The results of a study of the effect of KR on vaccination efficacy in poultry farming

| Group number | No chicken coop | Quantity (thousand) | MP application protocol |
| --- | --- | --- | --- |
| Control | 4 | 40.0 | KR was not given |
| Experimental Group 1 | 8 | 40.0 | 7 days of age for 3 days before vaccination with live viral vaccines |
| Experimental Group 2 | 7 | 40.0 | 1 day before vaccination against BNK |
| Experimental Group 3 | 5 | 40.0 | Within 3 days before vaccination and 7-10 days after vaccination against BNK |

Inspection conditions, microclimate parameters, light conditions, planting density, feeding conditions were the same in all groups according to the guidelines for growing POC 308 cross.

Immunity was determined at the age of 42 days in RHCA. At the same time, the clinical condition of the bird, the percentage of conservation, growth and feed costs were taken into account.

The results of the tests to determine the effectiveness of KR when vaccinating broilers against NCD are shown in table 8.

TABLE 8

The effect of KR on the effectiveness of vaccination against New Castle disease (NCD)

| Indicators | Control | Experimental Group 1 | Experimental Group 2 | Experimental Group 3 |
| --- | --- | --- | --- | --- |
| The average titer in emagglutination inhibition reaction (HIR) | 20 ± 8 | 38 ± 16 | 84 ± 28 | 124 ± 30* |
| Immunity Tension, % | 75 | 87.5 | 100 | 100 |

Note:
*$P < 0.05$,

The average titers of specific antibodies to the NCD virus both in the control and in the experimental groups were at the protective level. However, in the study of broiler sera at 42 days of age with the use of KR, a significant increase in the average titer in the experimental group 3 was established in comparison with the control by 6 times (<0.01). In the experimental groups (1,2), no significant difference in antibody titers was found in comparison with the control, however, they were at the level of protective and a tendency to increase this indicator by 1.8 and 4.3 times was found. Group immunity in the control was 75%, while in the experimental groups (3.4) 100%, in the 1st experimental group 87.5%. The death of broilers was in the control—9.8%, while the percentage of death decreased in the experimental groups: 2.8; 3.3 and 4 times, respectively, in comparison with the control. The average daily gains in the experimental groups ranged from 52-54 g, while in the control—48 g.

Therefore, we can conclude that the optimal use of KR for broilers in regions with a difficult epizootic situation with NCD is to use the drug at a dose of 0.03 ml/kg live weight for 3 days before vaccination and 7-10 days after vaccination against NCD. The use of the drug according to the above scheme leads to an increase in the average titer of specific antibodies to the NCD virus by 6 times and a decrease in the death of broilers by 4 times.

Pharmaceutical Compositions

Various methods of administering supramolecular combinatorial derivative peptides (UPCs) can be used. UPC composition can be given orally or can be administered by intravascular, subcutaneous, intraperitoneal injection, in the form of an aerosol, by ocular route of administration, into the bladder, topically, and so on. For example, inhalation methods are well known in the art. The dose of the therapeutic composition will vary widely depending on the particular antiviral UPC administered, the nature of the disease, the frequency of administration, the method of administration, the clearance of the agent used from the host, and the like. The initial dose may be higher with subsequent lower maintenance doses.

The dose can be administered with a frequency of once a week or once every two weeks, or divided into smaller doses and administered once or several times a day, twice a week, and so on to maintain an effective dose level. In many cases, a higher dose will be needed for oral administration than for intravenous administration. The compounds of this invention may be included in a variety of compositions for therapeutic administration. More specifically, the compounds of the present invention can be incorporated into pharmaceutical compositions in combination with suitable pharmaceutically acceptable carriers or diluents and may be included in solid, semi-solid, liquid or gaseous forms, such as capsules, powders, granules, ointments, creams, foams, solutions, suppositories, injections, forms for inhalation use, gels, microspheres, lotions and aerosols.

As such, the administration of the compounds can be carried out in various ways, including oral, buccal, rectal, parenteral, intraperitoneal, intradermal, transdermal, intratracheal administration and so on. The antiviral UPCs of the invention may be distributed systemically after administration or may be localized with using an implant or other composition that holds the active dose at the site of implantation. The compounds of the present invention may be administered alone, in combination with each other, or they may be used in combination with others known compounds (e.g. perforin, anti-inflammatory agents, and so on). In pharmaceutical dosage forms, the compounds may be administered in the form of their pharmaceutically acceptable salts. The following methods and excipients are given as examples only and are in no way limiting.

For preparations for oral administration, the compounds can be used alone or in combination with suitable additives for the manufacture of tablets, powders, granules or capsules, for example, with conventional additives such as lactose, mannitol, corn starch or potato starch; with binding agents such as crystalline cellulose, cellulose derivatives, gum arabic, corn starch or gelatins; with disintegrants such as corn starch, potato starch or gelatins; with disintegrants such as corn starch, potato starch or sodium carboxymethyl cellulose; with lubricants such as talc or magnesium stearate; and, if desired, with diluents, buffering agents, wetting agents, preservatives and flavoring agents. The compounds may be included in compositions for injection by dissolving, suspending or emulsifying them in an aqueous or non-aqueous solvent such as vegetable or other similar oils, synthetic aliphatic acid glycerides, esters of higher aliphatic acids or propylene glycol; and, if desired, with conventional additives such as solubilizers, isotonic agents, suspending agents, emulsifiers, stabilizers and preservatives.

The compounds can be used in an aerosol composition for inhalation administration. The compounds of the present invention can be incorporated into suitable pressure propellants such as dichlorodifluoromethane, propane, nitrogen and the like. In addition, the compounds can be incorporated into suppositories by mixing with a variety of bases, such as emulsifying bases or water-soluble bases. The compounds of the present invention can be administered rectally using a suppository. A suppository may contain excipients, such as cocoa butter, carboax, and polyethylene glycols, which melt at body temperature but are solid at room temperature. Standard dosage forms for oral or rectal administration, such as syrups, elixirs and suspensions, where each unit dose, can be made for example, a teaspoon, tablespoon, tablet or suppository, contains a predetermined amount of a composition containing one or more compounds of the present invention.

Similarly, unit dosage forms for injection or intravenous administration may contain a compound of the present invention in compositions in the form of a solution in sterile water, normal saline or another pharmaceutically acceptable carrier. Implants for sustained release of compositions are well known in the art. Implants are made in the form of microspheres, plates, and so on with biodegradable or non-biodegradable polymers. For example, lactic and/or glycolic acid polymers form a degradable polymer that is well tolerated by the host. An implant containing the antiviral combinatorial peptides of the invention is positioned close to the site of infection so that the local concentration of the active agent is increased compared to other areas of the body. As used herein, the term "unit dosage form" refers to physically discrete units suitable for use as single doses for human and animal subjects, each unit contains a predetermined number of compounds of the present invention, which, according to calculations, is sufficient to provide the desired effect, in conjunction with a pharmaceutically acceptable diluent, carrier or excipient.

The descriptions of the unit dosage forms of the present invention depend on the particular compound used, and the effect to be achieved, and the pharmacodynamics of the compound used in the host. Pharmaceutically acceptable excipients, such as excipients, adjuvants, carriers or diluents, are generally available. In addition, pharmaceutically acceptable excipients are generally available, such as pH adjusting agents and buffering agents, tonicity agents, stabilizers, wetting agents and the like. Typical doses for systemic administration range from 0.1 pg to 1000 milligrams per kg of subject body weight per administration. A typical dose may be one tablet for administration from two to six times a day, or one capsule or tablet with a sustained release for administration once a day with a proportionally higher content of the active ingredient. The effect of prolonged release may be due to the materials from which the capsule is made, which dissolve at different pH values, and capsules that provide slow release under the influence of osmotic pressure or any other known controlled release method. It will be clear to those skilled in the art that dose levels may vary depending on the particular connection, the severity of symptoms and the predisposition of the subject to side effects. Some of the specific compounds are more potent than others.

Preferred doses of this compound can be readily determined by those skilled in the art in a variety of ways. A preferred method is to measure the physiological activity of the compound. One of the methods of interest is the use of liposomes as a vehicle for delivery. Liposomes fuse with the cells of the target region and ensure the delivery of liposome contents into the cells. The contact of the liposomes with the cells is maintained for a time sufficient for fusion using various methods of maintaining contact, such as isolation, binding agents and the like. In one aspect of the invention, liposomes are designed to produce an aerosol for pulmonary administration. Liposomes can be made with purified proteins or peptides that mediate membrane fusion, such as Sendai virus or influenza virus and so on. Lipids can be any useful combination of known liposome forming lipids, including cationic or zwitterionic lipids, such as phosphatidylcholine.

The remaining lipids will usually be neutral or acidic lipids, such as cholesterol, phosphatidylserine, phosphatidylglycerol and the like. To obtain liposomes, the method described by Kato et al. (1991) J. Biol. Chem. 266: 3361. Briefly, lipids and a composition for incorporation into liposomes containing combinatorial supramolecular antibiotics are mixed in a suitable aqueous medium, suitable in a salt environment where the total solids content will be in the range of about 110% by weight. After vigorous stirring for short periods of approximately 5-60 seconds, the tube is placed in a warm water bath at approximately 25-40° C. and this cycle is repeated approximately 5-10 times. The composition is then sonicated for a suitable period of time, typically approximately 1-10 seconds, and optionally further mixed with a vortex mixer. Then the volume is increased by adding an aqueous medium, usually increasing the volume by about 1-2 times, followed by agitation and cooling. The method allows to include supramolecular structures with high total molecular weight in liposomes.

Compositions with Other Active Agents

For use in the methods under consideration, the antiviral SKP according to the invention can be included in compositions with other pharmaceutically active agents, in in particular other antiviral, antimicrobial or anticancer agents. Other agents of interest include a wide range of antiviral derivatives of mononucleotides and other RNA polymerase inhibitors known in the art. Classes of antiviral agents include interferons, lamivudine, ribavirin, etc. Other groups of antiviral agents include adefovir, wbacavir, didanosine, emtricitabine, lamivudine, stavudine, tenofovir, efavirenz, nevirapine, indinavir, lopinavir and ritonavir, nelfinavir, ritonavir, saquinavir, daclatasvir, sovofbuvir. Cytokines, for example, interferon gamma, tumor necrosis factor alpha, interleukin 12, and so on, may also be included in the composition of the UPC according to the invention. The present invention is further described by the following examples, which should not be construed as limiting the scope of the invention.

INDUSTRIAL APPLICABILITY

The invention relates to organic and bioorganic combinatorial chemistry, namely, to new combinatorial libraries of derivatives of oligopeptides and supramolecular structures based on them, which when used without separation into individual components have powerful antiviral properties. Thus obtained preparations are completely environmentally friendly, biodegradable and fully metabolizable both in the patient's body and in the environment, and the technology for their preparation belongs to the group of completely non-waste. The production of a patented product is feasible on existing equipment of pharmaceutical enterprises and does not require the development of new unique equipment, does not require energy and is waste-free and environmentally friendly.

The invention claimed is:

1. Combinatorial derivatives of an original oligopeptide with antiviral properties, wherein in the structure of the original oligopeptide are available for modification residues of amino groups of lysines, histidines, arginines, as well as alcohol residues of threonine and serine; wherein the original oligopeptide is simultaneously combinatorially modified by at least two different covalent modifiers and the resulting combinatorial mixture is used as an antiviral agent in various pharmaceutical compositions completely without purification and without isolation of each individual derivative, wherein the original oligopeptide is KKRKRKRKR (SEQ ID NO. 1) or KKRKSTRKR (SEQ ID. NO. 2).

2. The combinatorial derivatives of claim 1, wherein the molar ratio of the components of the combinatorial reaction is calculated according to the formulas:

$$k = n \times (2^n - 1) \qquad (1)$$

$$m = 4 \times (3 \times 2^{n-2} - 1) \qquad (2)$$

n=number of substitutional groups in the oligopeptide;
m=number of moles of the original oligopeptide and the number of different molecules of its combinatorial derivatives after synthesis;
k=the number of moles of each of the two modifiers in the combinatorial synthesis reaction to obtain the maximum number of different derivatives.

3. The combinatorial derivatives of claim 1, wherein the various covalent modifiers are anhydrides of at least two dicarboxylic acids.

4. The combinatorial derivatives of claim 1, wherein the different covalent modifiers are anhydrides of at least two tricarboxylic acids.

5. The combinatorial derivatives of claim 1, wherein the different covalent modifiers are at least one tricarboxylic acid anhydride and one dicarboxylic acid anhydride.

6. The combinatorial derivatives of claim 1, wherein the different covalent modifiers are at least two halogen derivatives.

7. The combinatorial derivatives of claim 1, wherein the different covalent modifiers are at least one halogen derivative and one dicarboxylic or tricarboxylic acid anhydride.

8. The combinatorial derivatives of claim 1, wherein the original oligopeptide is KKRKRKRKR (SEQ ID NO. 1).

* * * * *

SEQUENCE LISTING

<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: Synthetic Construct

<400> SEQUENCE: 1

Lys Lys Arg Lys Arg Lys Arg Lys Arg
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic Construct

<400> SEQUENCE: 2

Lys Lys Arg Lys Ser Thr Arg Lys Arg
1               5